United States Patent [19]

Kojima et al.

[11] 4,256,885

[45] Mar. 17, 1981

[54] PROCESS FOR THE PREPARATION OF 1-(2-TETRAHYDROFURYL)-5-FLUOROURACIL

[75] Inventors: Atsushi Kojima, Yokohama; Yoshitsugu Kohno, Omuta; Yoshimasa Ike, Yokohama; Tatsuro Yokoyama, Yokohama; Makoto Odate, Yokohama, all of Japan

[73] Assignee: Mitsui Toatsu Kagaku Kabushiki Kaisha, Tokyo, Japan

[21] Appl. No.: 749,433

[22] Filed: Dec. 10, 1976

[30] Foreign Application Priority Data

Dec. 24, 1975 [JP] Japan .................. 50/153403
Jan. 9, 1976 [JP] Japan .................... 51-1600
Jan. 22, 1976 [JP] Japan .................... 51-5408
May 20, 1976 [JP] Japan ................... 51-57255

[51] Int. Cl.$^3$ ........................................ C07D 405/04
[52] U.S. Cl. .................................................. 544/313
[58] Field of Search ........................ 260/260; 544/313

[56] References Cited

U.S. PATENT DOCUMENTS 3,960,864  6/1976  Townsend et al. ............... 260/260
4,107,162  8/1978  Suzuki et al. ..................... 544/313

OTHER PUBLICATIONS

Olah, Friedel—Crafts & Related Reactions, vol. 1, pp. 173–176, Pub. by Inerscience, (1963).
Brossmer et al., chemical abstracts, vol. 78, (1973), 58343r.

*Primary Examiner*—Paul M. Coughlan, Jr.
*Attorney, Agent, or Firm*—William J. Daniel

[57] ABSTRACT

A process for efficiently preparing 1-(2-tetrahydrofuryl)-5-fluorouracil useful as an antitumor agent or an antiviral agent which comprises reacting 5-fluorouracil with 2,3-dihydrofuran. This reaction proceeds advantageously in the presence of a reaction accelerator such as a Lewis acid in a polar solvent such as pyridine.

9 Claims, No Drawings

PROCESS FOR THE PREPARATION OF 1-(2-TETRAHYDROFURYL)-5-FLUOROURACIL

BACKGROUND OF THE INVENTION

The present invention relates to a new process for the preparation of 1-(2-tetrahydrofuryl)-5-fluorouracil. More particularly, the present invention relates to a process for the preparation of 1-(2-tetrahydrofuryl)-5-fluorouracil from 5-fluorouracil and 2,3-dihydrofuran.

The 1-(2-tetrahydrofuryl)-5-fluorouracil is a well known compound as an antitumor agent or an antiviral agent and several processes are known already for the preparation of this compound. For example, British Pat. No. 1,168,391 discloses a process wherein a mercury salt of 5-fluorouracil is reacted with 2-chlorotetrahydrofuran. Japanese patent Publn. No. 10510/Sho. 49 (1974) discloses a different process wherein 2,4-bis(-trimethylsilyl)-5-fluorouracil is reacted with 2-chlorotetrahydrofuran. Further, Belgian Pat. No. 807,556 discloses a still further process wherein 2,4-bis-(trimethylsilyl-5-fluorouracil is reacted with a 2-acyloxytetrahydrofuran or a 2-alkoxytetrahydrofuran.

However, the first process referred to above has several drawbacks in that the 2-chlorotetrahydrofuran used as a starting material for the reaction is extremely unstable, so that the reaction must be conducted at a low temperature ranging from $-60°$ C. to $-10°$ C. and, moreover, that the use of the mercury salt of 5-fluorouracil may cause environmental pollution. The second process is not only subject to the same industrial disadvantage mentioned before resulting from the use of 2-chlorotetrahydrofuran but also necessitates conversion of 5-fluorouracil into a reaction functional derivative thereof, i.e. 2,4-bis(trimethylsilyl-5-fluorouracil, thereby increasing the complexity of the process and increasing the cost of production. Finally, the third process referred to above cannot be said to be an industrially attractive, particularly because the use of 2,4-bis(trimethylsilyl)-5-fluorouracil makes the operation complicated as in the second process and the 2-acyloxytetrahydrofuran or 2-alkoxytetrahydrofuran used as a starting material must be prepared by adding a carboxylic acid or an alcohol to 2-chlorotetrahydrofuran.

Under these circumstances, there is a great demand in the relevant field for the development of an industrially operable process for efficiently preparing 1-(2-tetrahydrofuryl)-5-fluorouracil in a simple procedure from easily available starting materials without accompanying the formation of any harmful by-product.

BRIEF SUMMARY OF THE INVENTION

It is an object of the present invention to provide a new process for advantageously preparing 1-(2-tetrahydrofuryl)-5-fluorouracil.

It is another object of the present invention to provide a process for the preparation of 1-(2-tetrahydrofuryl)-5-fluorouracil directly from easily available 5-fluorouracil and 2,3-dihydrofuran.

It is still another object of the present invention to provide a process wherein 5-fluorouracil is efficiently reacted with 2,3-dihydrofuran.

Other and further objects, features and advantages of the invention will appear more fully from the following disclosure.

DETAILED DESCRIPTION OF THE INVENTION

In the present invention, 5-fluorouracil is reacted with 2,3-dihydrofuran to obtain 1-(2-tetrahydrofuryl)-5-fluorouracil. Both reactants are used in the present invention in such a proportion that 2,3-dihydrofuran is usually 1.0–4.0 mols, preferably 1.0–2.0 mols per mol of 5-fluorouracil.

The reaction temperature and the reaction time vary according to other reaction conditions but usually the reaction temperature is within a range from 80° C. to 200° C. and the reaction time within a range from about one hour to 20 hours.

This reaction may be carried out in the absence of a solvent but usually is carried out in the presence of a solvent, preferably a polar solvent. Illustrative of the solvent are, for example, dimethyl sulfoxide, dimethylformamide, dimethylacetamide, hexamethylphosphoramide, pyridine, picoline, quinoline, triethylamine, tetrahydrofuran, dioxane, acetone, methyl ethyl ketone and diisobutyl ketone.

The reaction of the present invention is generally carried out under atmospheric pressure. When a solvent is not used or its boiling point is low, however, the reaction may be carried out under superatmospheric pressure, for example, by using an autoclave. According to the present invention, the reaction can smoothly be carried out in the presence of a proper reaction accelerator whereby 1-(2-tetrahydrofuryl)-5-fluorouracil as the end product can be obtained selectively in a good yield. Typical examples of the reaction accelerator include:

(1) Amine salts

Illustrative of the amine salt are salts of organic amines with inorganic acids and organic acids, for example, hydrochlorides, hydrobromides, hydroiodides, sulfates, benzensulfonates, p-toluenesulfonates, acetates, and trifluoroacetates of methylamine, dimethylamine, triethylamine, pyridine, picoline, lutidine, quinoline and dimethylaniline. Quaternary ammonium salts such as N-pyridinium salts and tetramethylammonium salts can also be used equivalently. The amount of these amine salts is preferably 0.01 in molar proportion to 5-fluorouracil.

(2) A combination of an organic base and a metal halide

For example, pyridine, picoline, lutidine, quinoline, alkylamine, aniline and derivatives of these amines are adequate as the organic base, while chlorides such as aluminum chloride, titanium chloride, stannic chloride, zinc chloride, ferric chloride, cupric chloride, ferrous chloride, cuprous chloride, palladium chloride and platinum chloride, as well as bromides and fluorides corresponding to these chlorides are adequate as the metal halide. The use of such metal halide alone is low in reaction-accelerating effect, but the use of such metal halide jointly with the organic base synergistically serves to enhance the reaction-accelerating effect extremely significantly so that the yield of the end product exceeds 90%. No special limitation exists in the amounts of the organic base and the metal halide, but the amount of the metal halide used is preferably within a range of 0.001–10 mols per mol of 5-fluorouracil. The organic base is preferably used in an amount at least equivalent to the metal halide.

(3) Amphoteric compounds

Examples of the suitable amphoteric compound include amino acids such as glycin, alanine, β-alanine, lysine and proline; aminobenzenecarboxylic and aminobenzenesulfonic acids such as anthranilic acid, m-aminobenzoic acid, p-aminobenzoic acid, orthanilic acid, metanilic acid and sulfanilic acid; heterocyclic carboxylic and sulfonic acids such as nicotinic acid, isonicotinic acid, quinolinecarboxylic acid, pyrazinecarboxylic acid and pyridinesulfonic acid; and heterocyclic hydroxy compounds such as hydroxypyridine, hydroxypyrimidine, hydroxypyrazole and hydroxyquinoline. These amphoteric compounds are used in an amount of 0.1–10 mols per mol of 5-fluorouracil.

(4) Other reaction accelerators

Other effective reaction accelerators include ion exchange resins, metal chelates, onium compounds, Lewis acids, solid acidic catalysts and active carbon. Examples of the ion exchange resin include Amberlist 15 (trade name amine type, manufactured by Rohm & Haas Co.) and Amberlist A-27 (trade name Cl type, manufactured by Rohm & Haas Co.). Examples of the metal chelate include cupric disodium ethylenediaminetetracetate and cuprous N,N,N', N'-tetramethylethylene-diaminesulfate. Illustrative of the onium compound are, for example, dimethylphenylthionium perchlorate, and triethylthionium perchlorate. Illustrative of the Lewis acid are, for example, boron trifluoride, boron trifluoride etherate and tetrabutoxy titanium. Examples of the solid acidic catalyst include acid clay, kaolin, alumina, silica-magnesia, silica-alumina, molecular sieves, titanium oxide, aluminum oxide, nickel sulfate, aluminum sulfate and silver nitrate.

After completion of the reaction of the present invention, the reaction liquid is treated in any usual way to isolate the end product, i.e. 1-(2-tetrahydrofuryl)-5-fluorouracil. In the process of this invention, 1,3-bis(2-tetrahydrofuryl)-5-fluorouracil is formed in some cases as by-product, which is once separated as such or in the form of a mixture with the end product, i.e. 1-(2-tetrahydrofuryl)-5-fluorouracil and then subjected to a hydrolysis treatment to be converted into the end product. According to the present invention, therefore, 1-(2-tetrahydrofuryl)-5-fluorouracil can industrially advantageously be prepared in a very simple operation.

To further illustrate this invention, but not by way of limitation, the following examples are given.

EXAMPLE 1

In 20 ml of pyridine were dissolved 1.3 g of 5-fluorouracil. To this solution were added 1.4 g of 2,3-dihydrofuran and the mixture was reacted in an autoclave for 8 hours at 150° C. After completion of the reaction, pyridine was removed from the reaction liquid by distillation whereby 2.0 g of a residue were obtained. The residue was dissolved in 100 ml of chloroform under agitation and the solution was filtered to remove 0.15 g of insoluble matters. Chloroform was removed from the filtrate by distillation and the precipitated crystals were collected, washed with a small amount of benzene and dried whereby 1.55 g of white crystals were obtained which had a melting point of 165°–168° C. and was identical in IR-absorption spectra and NMR spectra with 1-(2-tetrahydrofuryl)-5-fluorouracil. A substance insoluble in chloroform was determined as the starting 5-fluorouracil. The yield of the end product was 88% based on the consumed 5-fluorouracil.

EXAMPLE 2

In 20 ml of dimethylformamide were dissolved 1.3 g of 5-fluorouracil. To this solution were added 1.4 g of 2,3-dihydrofuran and the mixture was reacted in an autoclave for 5 hours at 170° C. After completion of the reaction, the reaction liquid was treated in the same manner as described in Example 1 whereby 0.35 g of the starting 5-fluorouracil was recovered as a substance insoluble in chloroform and 1.20 g of 1-(2-tetrahydrofuryl)-5-fluorouracil were obtained. The yield of the end product was 82% based on the consumed 5-fluorouracil.

EXAMPLE 3

Into 30 ml of dioxane were suspended 1.3 g of 5-fluorouracil. To this suspension were added 1.4 g of 2,3-dihydrofuran and the mixture was reacted in an autoclave for 5 hours at 170° C. After completion of the reaction, the reaction liquid was treated in the same manner as described in Example 1 whereby 0.40 g of the starting 5-fluorouracil was recovered as a substance insoluble in chloroform and 1.10 g of 1-(2-tetrahydrofuryl)-5-fluorouracil was obtained. The yield of the end product was 79.5% based on the consumed 5-fluorouracil.

EXAMPLE 4

In 20 ml of dimethylacetamide were dissolved 1.3 g of 5-fluorouracil. To this solution were added 1.4 g of 2,3-dihydrofuran and the mixture was reacted in an autoclave for 5 hours at 180° C. After completion of the reaction, the reaction liquid was treated in the same manner as described in Example 1 whereby 0.22 g of the starting 5-fluorouracil was recovered as a substance insoluble in chloroform and 1.43 g of 1-(2-tetrahydrofuryl)-5-fluorouracil were obtained. The yield of the end product was 86.4% based on the consumed 5-fluorouracil.

EXAMPLE 5

Into 30 ml of tetrahydrofuran were suspended 1.3 g of 5-fluorouracil. To this suspension were added 1.4 g of 2,3-dihydrofuran and the mixture was reacted in an autoclave for 5 hours at 170° C. After completion of the reaction, the reaction liquid was treated in the same manner as described in Example 1 whereby 0.30 g of the starting 5-fluorouracil was recovered as a substance insoluble in chloroform and 1.28 g of 1-(2-tetrahydrofuryl)-5-fluorouracil were obtained. The yield of the end product was 83.2% based on the consumed 5-fluorouracil.

EXAMPLE 6

Into 30 ml of methyl ethyl ketone were suspended 1.3 g of 5-fluorouracil. To this suspension were added 1.4 g of 2,3-dihydrofuran and the mixture was reacted in an autoclave for 2 hours at 180° C. After completion of the reaction, the reaction liquid was treated in the same manner as described in Example 1 whereby 0.38 g of the starting 5-fluorouracil was recovered as a substance insoluble in chloroform and 1.12 g of 1-(2-tetrahydrofuryl)-5-fluorouracil were obtained. The yield of the end product was 79% based on the consumed 5-fluorouracil.

EXAMPLE 7

In 50 ml of pyridine were dissolved 2.5 g of 5-fluorouracil and 0.4 g of p-toluenesulfonic acid. To this solution were added 1.5 ml of 2,3-dihydrofuran and the mixture was reacted for 6 hours at 120° C. in an oil bath. Further, 3 ml of 2,3-dihydrofuran in 4 portions were added and the mixture was reacted for 15 hours. After completion of the reaction, pyridine was removed from the reaction liquid by distillation and the residue was dissolved in 100 ml of chloroform and filtered to separate insoluble matters. The filtrate was washed with water, dried and concentrated by removing chloroform by distillation. The precipitated crystals were collected by filtration, washed with a small amount of ether and dried to obtain 2.0 g of 1-(2-tetrahydrofuryl)-5-fluorouracil. The crystals had a melting point of 167°–168° C. and were identical in IR-absorption spectra with the standard sample.

The chloroform insoluble matters previously separated were washed with water to recover 0.67 g of the starting 5-fluorouracil. The yield of the end product was 71% based on the consumed 5-fluorouracil.

EXAMPLE 8

In 50 ml of pyridine were dissolved 2.5 g of 5-fluorouracil and 2.4 g of pyridine hydrochloride. To this solution were added 4.5 ml of 2,3-dihydrofuran in 4 portions and the mixture was reacted for 20 hours at 120° C. in an oil bath. After the reaction, a small amount of the reaction liquid was extracted and subjected to thin layer chromatography to check the state of preceeding of the reaction whereby the composition of the product was 90% of the end product, 5% of unreacted 5-fluorouracil and 5% of by-products. The reaction liquid was treated in the same manner as described in Example 7 to obtain 2.6 g of 1-(2-tetrahydrofuryl)-5-fluorouracil. The yield of the end product was 70% based on the initially used 5-fluorouracil.

EXAMPLE 9

In 20 ml of dimethylformamide were dissolved 1.3 g of 5-fluorouracil and 0.6 g of tetramethylammonium chloride. To this solution were added 2.25 ml of 2,3-tetrahydrofuran and the mixture was reacted in an autoclave for 9 hours at 150° C. After the reaction, dimethylformamide was removed from the reaction liquid and the residue was stirred together with chloroform and a small amount of water and filtered to separate insoluble matters. The chloroform layer of the filtrate was dried and concentrated and the precipitated crystals were collected by filtration. The crystals were washed with ether and dried to obtain 0.85 g of 1-(2-tetrahydrofuryl)-5-fluorouracil, which had a melting point of 165°–168° C. From the chloroform insoluble matters previously separated 0.5 g of the starting 5-fluorouracil were recovered. The yield of the end product was 69% based on the consumed 5-fluorouracil.

EXAMPLE 10

In 15 ml of dimethylformamide were dissolved 1.3 g of 5-fluorouracil and 1.8 g of N,N-dimethylaniline hydrochloride. To this solution were added 1.5 ml of 2,3-dihydrofuran and the mixture was reacted at 140° C. for 20 hours. After the reaction, dimethylformamide was removed from the reaction liquid by distillation and the residue was warmed for 30 minutes with 50 ml of ethanol containing 1% acetic acid. Then, ethanol was removed by distillation and the residue was stirred together with chloroform and water. The liquid mixture was separated and the chloroform layer was collected and dried. The chloroform was then distilled off to retain 1.5 g of 1-(2-tetrahydrofuryl)-5-fluorouracil. The yield of the end product was 75% based on the initially used 5-fluorouracil.

EXAMPLE 11

In 15 ml of dimethylformamide were dissolved 1.3 g of 5-fluorouracil and 0.41 g of triethylamine hydrochloride. To this solution were added 3 ml of 2,3-dihydrofuran and the mixture was reacted in an autoclave for 16 hours at 150° C. After the reaction, dimethylformamide was removed from the reaction liquid by distillation and the residue was treated in the same manner as described in Example 7 to obtain 0.8 g of 1-(2-tetrahydrofuryl)-5-fluorouracil. From the chloroform insoluble matter 0.6 g of the starting 5-fluorouracil was recovered. The yield of the end product was 74% based on the consumed 5-fluorouracil.

EXAMPLE 12

In 50 ml of pyridine were dissolved 2.5 g of 5-fluorouracil and 0.35 g of anhydrous aluminum chloride. To this solution were added 2.3 ml of 2,3-dihydrofuran and the mixture was reacted at 120° C. for 6 hours. A part of the reaction liquid was extracted and subjected to thin layer chromatography to observe the state of proceeding of the reaction whereby the composition of the product was 70% of the end product, 10% of by-products and less than 1% of unreacted 5-fluorouracil. The pyridine was distilled off from the reaction liquid and the residue was shaken with 50 ml of chloroform and a small amount of water and the mixture was separated. The chloroform layer was dried and the chloroform was distilled off. The precipitated crystals were collected by filtration, washed with ether and dried to obtain 2.9 g of 1-(2-tetrahydrofuryl)-5-fluorouracil in a yield of 75.4%, which had a melting point of 167°–168° C.

The IR-absorption spectra of the crystals were quite identical with those of the standard sample.

EXAMPLE 13

In 40 ml of pyridine were dissolved 5.2 g of 5-fluorouracil. The solution was ice cooled and 0.8 g of titanium tetrachloride was added thereto. Then, 6 ml of 2,3-dihydrofuran in 20 ml of pyridine were added to the mixture in 1.5 hours while stirring it at 80° C. The reaction was continued for 4 hours. After completion of the reaction, pyridine was removed from the reaction liquid by distillation and 500 ml of chloroform and 5 g of silica gel were added to the residue. The mixture was decolored and filtered and the filtrate was concentrated to obtain 5.5 g of 1-(2-tetrahydrofuryl)-5-fluorouracil in a yield of 69%.

EXAMPLE 14

In 50 ml of pyridine were dissolved 2.5 g of 5-fluorouracil and 0.64 g of ferric chloride. The reaction was carried out at 120° C. for 8 hours while adding 2.3 ml of 2,3-dihydrofuran to the solution. The reaction liquid was treated in the same manner as described in Example 12 to obtain 1.8 g of 1-(2-tetrahydrofuryl)-5-fluorouracil. From the aqueous layer 0.8 g of unreacted 5-fluorouracil was recovered. The yield of the end product was 69% based on the consumed 5-fluorouracil.

EXAMPLE 15

In 30 ml of dimethylformamide were dissolved 2.6 g of 5-fluorouracil, 2.66 g of anhydrous aluminum chloride and 7.0 ml of triethylamine. The reaction was carried out at 130° C. for 6 hours while adding 3.0 ml of 2,3-dihydrofuran to the solution. The reaction liquid was treated in the same manner as described in Example 13 to obtain 2.4 g of (1-(2-tetrahydrofuryl)-5-fluorouracil. The yield was 60%.

EXAMPLE 16

In 30 ml of dimethylformamide were dissolved 2.6 g of 5-fluorouracil and 0.246 g of nicotinic acid. 2.8 Grams of 2,3-dihydrofuran in several portions were added in 4 hours to the solution while heating it at 140° C. The mixture was then reacted for 4 hours at the same temperature. After completion of the reaction, dimethylformamide was distilled off from the reaction liquid and 50 ml of chloroform were added to the residue. After stirring, the solution was filtered to remove insoluble matters and the filrate was washed with water and dried over anhydrous sodium sulfate. Then, chloroform was distilled off from the dried filtrate to obtain 1.85 g of 1-(2-tetrahydrofuryl)-5-fluorouracil which had a melting point of 165°–168° C. The chloroform insoluble matters were 5-fluorouracil containing 0.24 g of nicotinic acid. The yield of the end product was 61% based on the consumed 5-fluorouracil.

EXAMPLE 17

In 20 ml of dimethylformamide were dissolved 1.3 g of 5-fluorouracil and 0.75 g of glycin. 2.8 Grams of 2,3-dihydrofuran in several portions were added in 8 hours to the solution while heating it at 145° C. The mixture was then reacted for 5 hours at the same temperature. After completion of the reaction, the reaction liquid was treated in the same manner as described in Example 16. 0.9 g of 1-(2-tetrahydrofuryl)-5-fluorouracil was obtained and 1.0 g of 5-fluorouracil containing 0.75 g of glycin was recovered. The yield of the end product was 56% based on the consumed 5-fluorouracil.

EXAMPLE 18

To 50 ml of dimethylformamide were added 2.6 g of 5-fluorouracil, 2.6 g of Amberlist A-27 (Cl type) and then 3.5 g of 2,3-dihydrofuran. The mixture was reacted at 130° C. for 7 hours. Insoluble matters were removed from the reaction liquid and the solvent was distilled off under reduced pressure. The residue was dissolved in chloroform and a small amount of water and the chloroform layer was separated and dried. The chloroform was distilled off and the residue was recrystallized from ethanol whereby 2.5 g of 1-(2-tetrahydrofuryl)-5-fluorouracil were obtained. The yield was 62.5%. This product was a melting point of 166°–168° C. and its IR-absorption spectra were identical with those of the standard sample.

EXAMPLE 19

In 10 ml of pyridine were dissolved 0.39 g of 5-fluorouracil and 0.42 g of 2,3-dihydrofuran. To the solution were added 72 mg of dimethylphenylsulfonium perchlorate and the mixture was reacted for 5 hours at 130° C. After the reaction, pyridine was distilled off under reduced pressure and 20 ml of water were added to the residue. The aqueous solution was treated with caustic soda to have a pH value of 10–11 and then washed with 20 ml of chloroform. The aqueous alkaline solution was treated while cold with diluted hydrochloric acid to adjust the pH value of the solution to 3.5 and then extracted three times with 20 ml of chloroform. The chloroform extract was dried and then the chloroform was distilled off. The residue was recrystallized from ethanol to obtain 0.35 g of 1-(2-tetrahydrofuryl)-5-fluorouracil. The yield was 58.3%.

EXAMPLE 20

In 10 ml dimethylformamide were dissolved 0.39 g of 5-fluorouracil and 0.42 g of 2,3-dihydrofuran. To the solution was added 0.204 g of tetrabutoxytitanium and the mixture was reacted at 130°
C. for 5 hours. After the reaction, the solvent was distilled off and 20 ml of water were added to the residue. The aqueous solution was treated with caustic soda to have a pH value of 10–11 and then warmed at
60° C. After removing insoluble titanic acid by filtration, the aqueous solution was treated with diluted hydrochloric acid to adjust the pH value of the solution to 3.5 and extracted with chloroform. The extract was then treated in the same manner as described in Example 19 to obtain 0.44 g of 1-(2-tetrahydrofuryl)-5-fluorouracil. The yield was 73.3%.

EXAMPLE 21

In 100 ml of pyridine were dissolved 13.0 g of 5-fluorouracil and 10.5 g of 2,3-dihydrofuran. To the solution were added 7.5 g of alumina and the mixture was reacted at 130° C. for 24 hours. After completion of the reaction, the reaction liquid was filtered to remove the catalyst and the solvent was distilled off. The residue was dissolved in chloroform to recover 3.04 g of insoluble unreacted 5-fluorouracil. The chloroform was distilled off from the chloroform layer and the residue was recrystallized from ethanol to give 13.52 g of 1-(2-tetrahydrofuryl)-5-fluorouracil. The yield of the end product was 88.9% based on the consumed 5-fluorouracil.

EXAMPLE 22

In 100 ml of pyridine were dissolved 13.0 g of 5-fluorouracil and 10.5 g of 2,3-dihydrofuran. To the solution were added 7.5 g of acid clay and the mixture was reacted at 130° C. for 10 hours. The reaction liquid was treated in the same manner as described in Example 21 whereby 1.65 g of 5-fluorouracil were recovered and 14.30 g of 1-(2-tetrahydrofuryl)-5-fluorouracil were obtained. The yield of the end product was 81.9% based on the consumed 5-fluorouracil.

EXAMPLE 23

In 10 ml of β-picolin were dissolved 0.39 g of 5-fluorouracil and 0.42 g of 2,3-dihydrofuran. To the solution was added 0.102 g of silver nitrate and the mixture was then reacted at 140° C. for 5 hours. The reaction liquid was treated in the same manner as described in Example 21 whereby 0.46 g of 1-(2-tetrahydrofuryl)-5-fluorouracil was obtained. The yield was 76.6%.

EXAMPLE 24

In 10 ml of α-picoline were dissolved 0.39 g of 5-fluorouracil and 0.42 g of 2,3-dihydrofuran. To the solution was added 0.30 g of cupric disodium ethylenediaminetetracetate and the mixture was then reacted at 150° C. for 5 hours. The reaction liquid was treated in the same manner as described in Example 21 whereby 0.38 g of 1-(2-tetrahydrofuryl)-5-fluorouracil was obtained. The yield was 63.3%.

EXAMPLE 25

In 10 ml of pyridine were dissolved 0.34 g of 5-fluorouracil and 0.42 g of 2,3-dihydrofuran. To the solution was added 0.3 g of active carbon and the mixture was then reacted at 130° C. for 8 hours. After the reaction, the active carbon was separated and the solvent was distilled off under reduced pressure. Chloroform and a small amount of water were added to the residue and the mixture was stirred and separated. The chloroform layer was dried and the chloroform was distilled off whereby 0.43 g of 1-(2-tetrahydrofuryl)-5-fluorouracil was obtained. The yield was 72%.

It is understood that the preceeding representative examples may be varied within the scope of the present specification, as to reaction accelerators, polar solvents and reaction conditions, by one skilled in the art to achieve essentially the same results.

As many apparently widely different embodiments of this invention may be made without departing from the spirit and scope theeof, it is to be understood that this invention is not limited to the specific embodiments thereof except as defined in the appended claims.

What is claimed is:

1. A method for producing 1-(2-tetrahydrofuryl)-5-fluorouracil which comprises heating a reacting mixture comprising 5-fluorouracil and 2,3-dihydrofurane in the pressure of a reaction accelerator selected from the group consisting of an amine salt, a mixture of an organic base and a metal halide, an amphoteric compound, an ion exchange resin, a metal chelate, an onium compound, a Lewis acid selected from the group consisting of boron trifluoride, boron trifluoride etherate and tetrabutoxy titaniu, a solid acidic catalyst selected from the group consisting of acid clay, kaolin, alumina, silica-magnesia, silica-alumina, molecular sieves, titanium oxide, nickel sulfate, aluminum sulfate and silver nitrate, and active carbon.

2. A process according to claim 1 wherein 2,3-dihydroxyfuran is used in an amount of 1.0–4.0 mols per mole of 5-fluorouracil.

3. A process according to claim 1 wherein said polar solvent is at least one selected from the group consisting of dimethyl sulfoxide, dimethylformamide, dimethylacetamide, hexamethylphosphoramide, pyridine, quinoline, triethylamine, tetrahydrofuran, dioxane, acetone, methyl ethyl ketone and diisobutyl ketone.

4. A process according to claim 1 wherein said reaction accelerator is an amine salt and is a salt of an organic amine with an inorganic or organic acid or a quanternary ammonium salt.

5. A process according to claim 1 wherein said reaction accelerator is an amine salt and is a hydrochloride, hydrobromide, hydroiodide, benzenesulfonate, p-toluenesulfonate, acetate or trifluoroacetate of methylamine, dimethylamine, triethylamine, pyridine, picoline, lutidine, quinoline or dimethylaniline or is N-methylpyridinium salt or tetramethylammonium salt.

6. A process according to claim 1 wherein said reaction accelerator is said mixture of an organic base and a metal halide wherein said organic base is one of pyridine, picoline, lutidine, quinoline, alkylamine, aniline and derivatives thereof and said metal halide is one of aluminum chloride, titanium tetrachloride, stannic chloride, zinc chloride, ferric chloride, cupric chloride, ferrous chloride, cuprous chloride, palladium chloride and platinum chloride, as well as metal bromides and fluorides corresponding to these metal chlorides.

7. A process according to claim 1 wherein said reaction accelerator is an amphoteric compound and is one of amino acids, aminobenzenecarboxylic and aminobenzenesulfonic acids and heterocyclic carboxylic and sulfonic acids and heterocyclic hydroxy compounds.

8. A process according to claim 7 wherein said reaction accelerator is an amino acid selected from the group consisting of glycin or alanine.

9. A process according to claim 1 wherein said reaction is carried out under atmospheric pressure at a temperature in the range of 80°–200° C.

* * * * *